(12) United States Patent
Doi

(10) Patent No.: US 9,786,047 B2
(45) Date of Patent: Oct. 10, 2017

(54) INFORMATION PROCESSING SYSTEM, METHOD, AND APPARATUS SUPPORTING A PATHOLOGICAL DIAGNOSIS, AND CONTROL METHOD AND CONTROL PROGRAM THEREOF

(75) Inventor: Shun Doi, Tokyo (JP)

(73) Assignee: NEC Corporation, Tokyo (JP)

(*) Notice: Subject to any disclaimer, the term of this patent is extended or adjusted under 35 U.S.C. 154(b) by 91 days.

(21) Appl. No.: 14/117,400

(22) PCT Filed: May 7, 2012

(86) PCT No.: PCT/JP2012/002982
§ 371 (c)(1),
(2), (4) Date: Nov. 13, 2013

(87) PCT Pub. No.: WO2012/157201
PCT Pub. Date: Nov. 22, 2012

(65) Prior Publication Data
US 2014/0314287 A1  Oct. 23, 2014

(30) Foreign Application Priority Data

May 18, 2011  (JP) ................ 2011-111707

(51) Int. Cl.
*G06K 9/00* (2006.01)
*G06T 7/00* (2017.01)
*G06F 19/00* (2011.01)

(52) U.S. Cl.
CPC .......... *G06T 7/0012* (2013.01); *G06F 19/321* (2013.01); *G06K 9/00127* (2013.01)

(58) Field of Classification Search
None
See application file for complete search history.

(56) References Cited

U.S. PATENT DOCUMENTS 5,677,966 A * 10/1997 Doerrer .............. G01N 15/1475
                                                       382/128
5,987,345 A * 11/1999 Engelmann .......... G06F 19/321
                                                       128/920

(Continued)

FOREIGN PATENT DOCUMENTS

JP  10-197522  7/1998
JP  2006-153742  6/2006

(Continued)

OTHER PUBLICATIONS

C. Dean and C. Ilvento. "Improved Cancer Detection Using Computer-Aided Detection with Diagnostic and Screening Mammography: Prospective Study of 104 Cancers", AJR Women's Imaging, Jul. 2006.*

(Continued)

*Primary Examiner* — Vu Le
*Assistant Examiner* — Samah Beg
(74) *Attorney, Agent, or Firm* — Finnegan, Henderson, Farabow, Garrett & Dunner, L.L.P.

(57) ABSTRACT

An information processing system, which supports a pathological diagnosis based on a tissue sample image which is obtained by imaging a body tissue, is provided, and the system includes: a pathological diagnosis unit (110) which performs a pathological diagnosis based on the tissue sample image and outputs a first pathological diagnosis result; an input unit (120) which inputs a second pathological diagnosis result obtained by a pathological diagnosis performed by a pathologist based on the tissue sample image; and an output unit (130) which outputs information necessary for a post process corresponding to combination of the first pathological diagnosis result and the second pathological diagnosis result.

10 Claims, 16 Drawing Sheets

(56) References Cited

U.S. PATENT DOCUMENTS

| | | | |
|---|---|---|---|
| 6,078,680 A * | 6/2000 | Yoshida | G06T 7/0012 382/128 |
| 6,252,979 B1 * | 6/2001 | Lee | G06K 9/00127 359/382 |
| 6,393,157 B1 * | 5/2002 | Miller | G06T 7/0081 382/254 |
| 6,430,309 B1 * | 8/2002 | Pressman | G01N 15/1468 128/920 |
| 6,826,552 B1 * | 11/2004 | Grosser | G06Q 30/02 706/45 |
| 6,988,088 B1 * | 1/2006 | Miikkulainen | G06F 19/345 706/14 |
| 7,209,835 B1 * | 4/2007 | Pearlman | G06F 19/3437 702/19 |
| 7,228,315 B2 * | 6/2007 | Finitzo | A61B 5/04845 |
| 7,493,299 B2 * | 2/2009 | Entwistle | G06N 5/022 706/45 |
| 7,529,394 B2 * | 5/2009 | Krishnan et al. | 382/128 |
| 8,064,663 B2 * | 11/2011 | Van Hoe et al. | 382/128 |
| 9,042,616 B2 * | 5/2015 | Goto | A61B 5/055 378/4 |
| 9,230,154 B2 * | 1/2016 | Kiyuna | G06F 19/321 |
| 2002/0131625 A1 * | 9/2002 | Vining et al. | 382/128 |
| 2002/0194019 A1 * | 12/2002 | Evertsz | G06F 17/3028 705/2 |
| 2004/0120557 A1 * | 6/2004 | Sabol | G06Q 10/10 382/128 |
| 2006/0050947 A1 * | 3/2006 | Petrou et al. | 382/133 |
| 2006/0115146 A1 | 6/2006 | Ogura et al. | |
| 2006/0173266 A1 * | 8/2006 | Pawluczyk | G01N 21/64 600/407 |
| 2007/0019854 A1 * | 1/2007 | Gholap | G06T 7/0012 382/133 |
| 2007/0122017 A1 * | 5/2007 | Binnig | G06K 9/00127 382/128 |
| 2007/0264635 A1 | 11/2007 | Suzuki et al. | |
| 2009/0070143 A1 * | 3/2009 | Haider | 705/3 |
| 2009/0116723 A1 * | 5/2009 | Okajima et al. | 382/133 |
| 2009/0185731 A1 * | 7/2009 | Ray | G06T 7/0012 382/131 |
| 2010/0098306 A1 * | 4/2010 | Madabhushi | G06K 9/0014 382/128 |
| 2010/0256459 A1 * | 10/2010 | Miyasa | G06Q 50/22 600/300 |
| 2010/0256991 A1 * | 10/2010 | Ishikawa | G06F 19/321 705/3 |
| 2011/0142301 A1 * | 6/2011 | Boroczky | G06T 7/0012 382/128 |
| 2012/0004514 A1 * | 1/2012 | Marugame | 600/300 |
| 2012/0327211 A1 * | 12/2012 | Yamamoto | 348/79 |
| 2013/0208950 A1 * | 8/2013 | Athelogou | G06T 7/0012 382/107 |
| 2014/0122515 A1 * | 5/2014 | Lee | G06F 17/30477 707/758 |
| 2015/0019259 A1 * | 1/2015 | Qureshi | G06F 19/3481 705/3 |

FOREIGN PATENT DOCUMENTS

| | | |
|---|---|---|
| JP | 2009-148269 | 7/2009 |
| JP | 2010-281636 | 12/2010 |

OTHER PUBLICATIONS

International Search Report mailed Jun. 5, 2012.

* cited by examiner

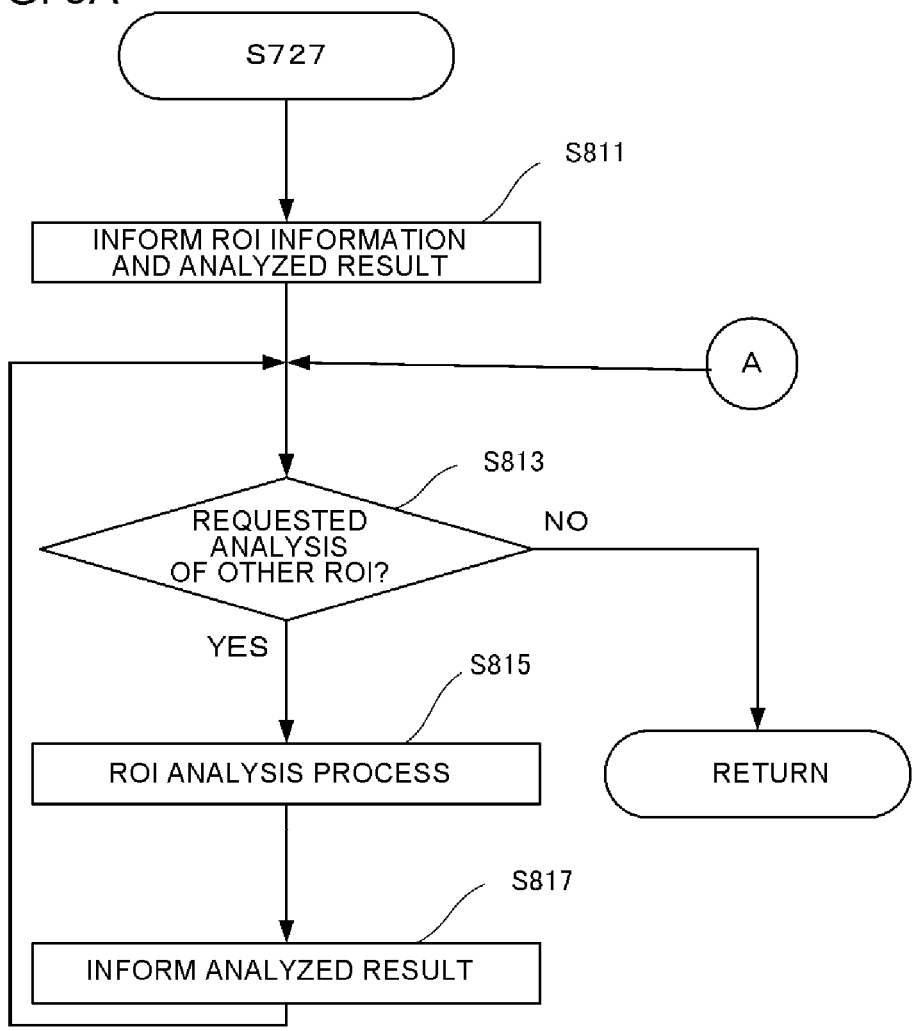

FIG. 10

| PATHOLOGIST ID | SITE | DIAGNOSIS DATE | PATHOLOGIST DIAGNOSIS RESULT | AUTOMATIC DIAGNOSIS RESULT | FINAL RESULT | PATHOLOGIST ROI | AUTOMATIC ROI | FINAL ROI | EVALUATION VALUE |
|---|---|---|---|---|---|---|---|---|---|
| PA001 | BREAST | ... | | | | | | | |
| | LUNG | ... | | | | | | | |
| PA002 | | | | | | | | | |

INFORMATION PROCESSING SYSTEM, METHOD, AND APPARATUS SUPPORTING A PATHOLOGICAL DIAGNOSIS, AND CONTROL METHOD AND CONTROL PROGRAM THEREOF

CROSS-REFERENCE TO RELATED PATENT APPLICATIONS

This application is a National Stage Entry of International Application No. PCT/JP2012/002982, filed May 7, 2012, which claims priority from Japanese Patent Application No. 2011-111707, filed May 18, 2011. The entire contents of the above-referenced applications are expressly incorporated herein by reference.

TECHNICAL FIELD

The present invention relates to an information processing technology for supporting a diagnosis based on a tissue sample image of a body tissue.

BACKGROUND ART

In the above technological field, as a pathological diagnosis supporting method, Patent Document 1 discloses a technology for notifying of a diagnosis category having high fitness based on an amount of characteristics of a tissue image. In addition, as a pathological diagnosis by an apparatus, Patent Document 2 discloses a technology for analyzing a pathological tissue image with an apparatus.

RELATED DOCUMENT

Patent Document

[Patent Document 1] Japanese Unexamined Patent Application Publication No. H10-197522
[Patent Document 2] Japanese Unexamined Patent Application Publication No. 2010-281636

DISCLOSURE OF THE INVENTION

However, in the related art, a pathologist only refers to a diagnosis category or an analysis result presented by an apparatus. The inventor has considered improving accuracy of diagnosis by evaluating a diagnosis result of a pathologist using a system.

An object of the present invention is to provide a technology for solving the aforementioned problems.

To achieve the object, according to the present invention, there is provided an information processing system which supports a pathological diagnosis based on a tissue sample image which is obtained by imaging a body tissue, the system including: a pathological diagnosis unit which performs a pathological diagnosis based on the tissue sample image and outputs a first pathological diagnosis result; an input unit which inputs a second pathological diagnosis result obtained by a pathological diagnosis performed by a pathologist based on the tissue sample image; and an output unit which outputs information necessary for a post process corresponding to combination of the first pathological diagnosis result and the second pathological diagnosis result.

To achieve the object, there is provided an information processing method which supports a pathological diagnosis based on a tissue sample image which is obtained by imaging a body tissue, the method including: a pathological diagnosis step of performing a pathological diagnosis based on the tissue sample image and outputting a first pathological diagnosis result; an input step of inputting a second pathological diagnosis result obtained by a pathological diagnosis performed by a pathologist based on the tissue sample image; and an output step of outputting information necessary for a post process corresponding to combination of the first pathological diagnosis result and the second pathological diagnosis result.

To achieve the object, there is provided an information processing apparatus which supports a pathological diagnosis based on a tissue sample image which is obtained by imaging a body tissue, the method including: a pathological diagnosis unit which performs a pathological diagnosis based on the tissue sample image and outputs a first pathological diagnosis result; a reception unit which receives a second pathological diagnosis result obtained by a pathological diagnosis performed by a pathologist based on the tissue sample image; and a transmission unit which transmits information necessary for a post process corresponding to combination of the first pathological diagnosis result and the second pathological diagnosis result.

To achieve the object, there is provided a control method of a pathological diagnosis supporting apparatus which supports a pathological diagnosis based on a tissue sample image which is obtained by imaging a body tissue, the method including: a pathological diagnosis step of performing a pathological diagnosis based on the tissue sample image and outputting a first pathological diagnosis result; a reception step of receiving a second pathological diagnosis result obtained by a pathological diagnosis performed by a pathologist based on the tissue sample image; and a transmission step of transmitting information necessary for a post process corresponding to combination of the first pathological diagnosis result and the second pathological diagnosis result.

To achieve the object, there is provided a control program of an information processing apparatus which supports a pathological diagnosis based on a tissue sample image which is obtained by imaging a body tissue, the program which causes a computer to execute: a pathological diagnosis step of performing a pathological diagnosis based on the tissue sample image and outputting a first pathological diagnosis result; a reception step of receiving a second pathological diagnosis result obtained by a pathological diagnosis performed by a pathologist based on the tissue sample image, and a transmission step of transmitting information necessary for a post process corresponding to combination of the first pathological diagnosis result and the second pathological diagnosis result.

According to the present invention, the system can evaluate the result of the pathological diagnosis that a pathologist performed based on the body tissue image.

BRIEF DESCRIPTION OF THE DRAWINGS

The objects described above, the other objects, characteristics and advantages will become clearer with preferred exemplary embodiments which will be described later and the following drawings attached thereto.

FIG. 8A is a flowchart showing a process sequence of a malignancy measurement process according to the second exemplary embodiment of the present invention.

FIG. 10 is a view showing a configuration of pathologist diagnosis tendency information according to the third exemplary embodiment of the present invention.

DESCRIPTION OF EMBODIMENTS

Hereinafter, the exemplary embodiments of the present invention will be described in detail as examples, with reference to the drawings. However, constituent elements described in the following exemplary embodiments are only examples and a technical scope is not limited thereto.

First Exemplary Embodiment

An information processing system 100 as a first exemplary embodiment of the present invention will be described using FIG. 1. The information processing system 100 is a system that supports a pathological diagnosis based on a tissue sample image obtained by imaging a body tissue.

Figure 1:
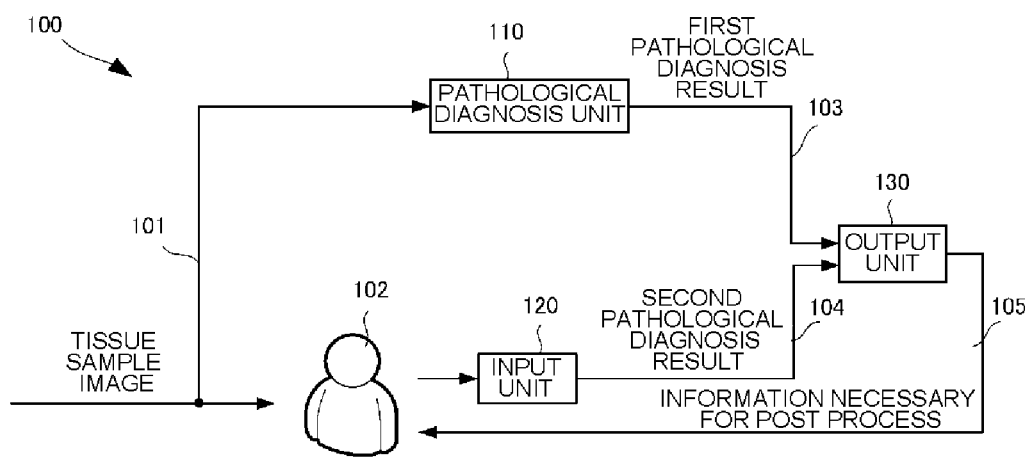
FIG. 1 is a block diagram showing a configuration of an information processing system according to a first exemplary embodiment of the present invention.

As described in FIG. 1, the information processing system 100 includes a pathological diagnosis unit 110, an input unit 120, and an output unit 130. The pathological diagnosis unit 110 performs a pathological diagnosis based on a tissue sample image 101, and outputs a first pathological diagnosis result 103. The input unit 120 inputs a second pathological diagnosis result 104 obtained by the pathological diagnosis that a pathologist 102 performs based on the tissue sample image 101. The output unit 130 outputs information 105 necessary for a post process corresponding to a combination of the first pathological diagnosis result 103 and the second pathological diagnosis result 104.

According to the exemplary embodiment, the result of the pathological diagnosis, which is performed by a pathologist based on the body tissue image, can be evaluated with a system.

Second Exemplary Embodiment

Next, an information processing system according to a second exemplary embodiment of the present invention will be described. In the exemplary embodiment, a pathological diagnosis result of a pathologist and a pathological diagnosis result obtained by an information processing apparatus are compared, and information of a post process corresponding to a compared result is informed to a pathologist. According to the exemplary embodiment, a pathologist can rapidly obtain a final diagnosis result using the compared result and the information of the post process.

<<Configuration of Information Processing System>>

Figure 2:
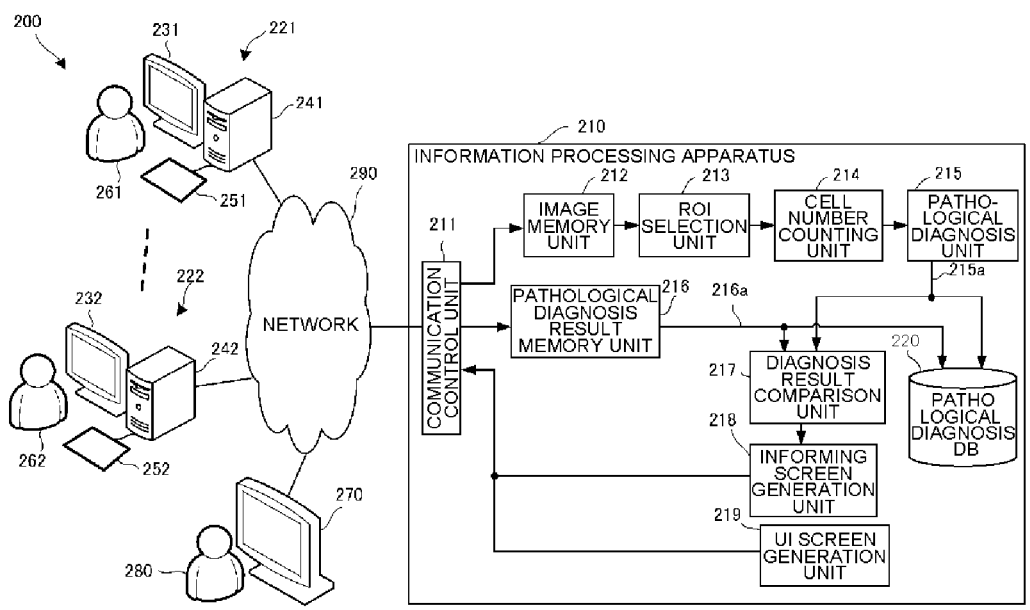
FIG. 2 is a block diagram showing a configuration of an information processing system according to a second exemplary embodiment of the present invention.

FIG. 2 is a block diagram showing a configuration of the information processing system according to the exemplary embodiment.

In FIG. 2, an information processing apparatus 210 functions as a pathological diagnosis supporting apparatus, which supports a pathological diagnosis that a pathologist 261 or 262 performs based on a body tissue sample image. The information processing apparatus 210 includes the following functional units. In addition, the functions included in the pathological diagnosis unit 110 of FIG. 1 of the first exemplary embodiment are, for example, implemented with a communication control unit 211, an image memory unit 212, an ROI selection unit 213, a cell counting unit 214, a pathological diagnosis unit 215, a pathological diagnosis result memory unit 216, and a diagnosis result comparison unit 217 of the exemplary embodiment. The function included in the input unit 120 of FIG. 1 is, for example, implemented with the communication control unit 211 of the exemplary embodiment. Further, the function included in the output unit 130 of FIG. 1 is implemented with the communication control unit 211, an informing screen generation unit 218, and a UI screen generation unit 219 of the exemplary embodiment.

The information processing apparatus includes the communication control unit 211 that receives a body tissue sample image through a network 290, and transmits screen information through the network. The information processing apparatus includes the image memory unit 212 that stores the received body tissue sample image. The information processing apparatus includes the ROI selection unit 213 that selects a region of interest (ROI) in the body tissue sample image to be diagnosed. The information processing apparatus includes the cell number counting unit 214 that finds cancer cells in the ROI and counts the number thereof. In addition, the information processing apparatus includes the pathological diagnosis unit 215 that performs pathological diagnosis based on the counted number of the cells in each ROI. On the other hand, the information processing apparatus includes the pathological diagnosis result memory unit 216 that stores a pathological diagnosis result of a pathologist diagnosed in the communication control unit 211 through the network 290.

The information processing apparatus includes the diagnosis result comparison unit 217 that compares a diagnosis result 215a, which is obtained from the information processing apparatus 210 output from the pathological diagnosis unit 215, and a diagnosis result 216*a*, which is a diagnosis result of the pathological diagnosis and stored in the result memory unit 216. The information processing apparatus includes the informing screen generation unit 218 that generates an informing screen for informing a pathologist, which screen corresponds to the comparing result of the diagnosis result comparison unit 217. The information processing apparatus includes the UI screen generation unit 219 that generates a screen used as a user interface (UI) for a pathologist. In addition, the information processing apparatus includes a pathological diagnosis DB 220 which accumulates the diagnosis results 215*a* obtained by the information processing apparatus 210 in association with the diagnosis result 216*a* which is the diagnosis result of a pathologist.

An information processing system 200 of FIG. 2 includes a plurality of pathologist terminals 221 and 222 which transmit a body tissue sample image to the information processing apparatus 210 through the network 290. The pathologist terminals 221 and 222 include display devices 231 and 232, computers 241 and 242, and scanners 251 and 252, respectively. In addition, the information processing system includes a specialist terminal 270 in which a body tissue sample image is displayed by a specialist 280 who performs pathological diagnosis on behalf of a pathologist or with a pathologist.

The number of pathologist terminals connected to the network is not limited. In addition, the terminals connected to the network are not limited to those described in FIG. 2.

<<Operation Sequence of Information Processing System>>

Figure 3:
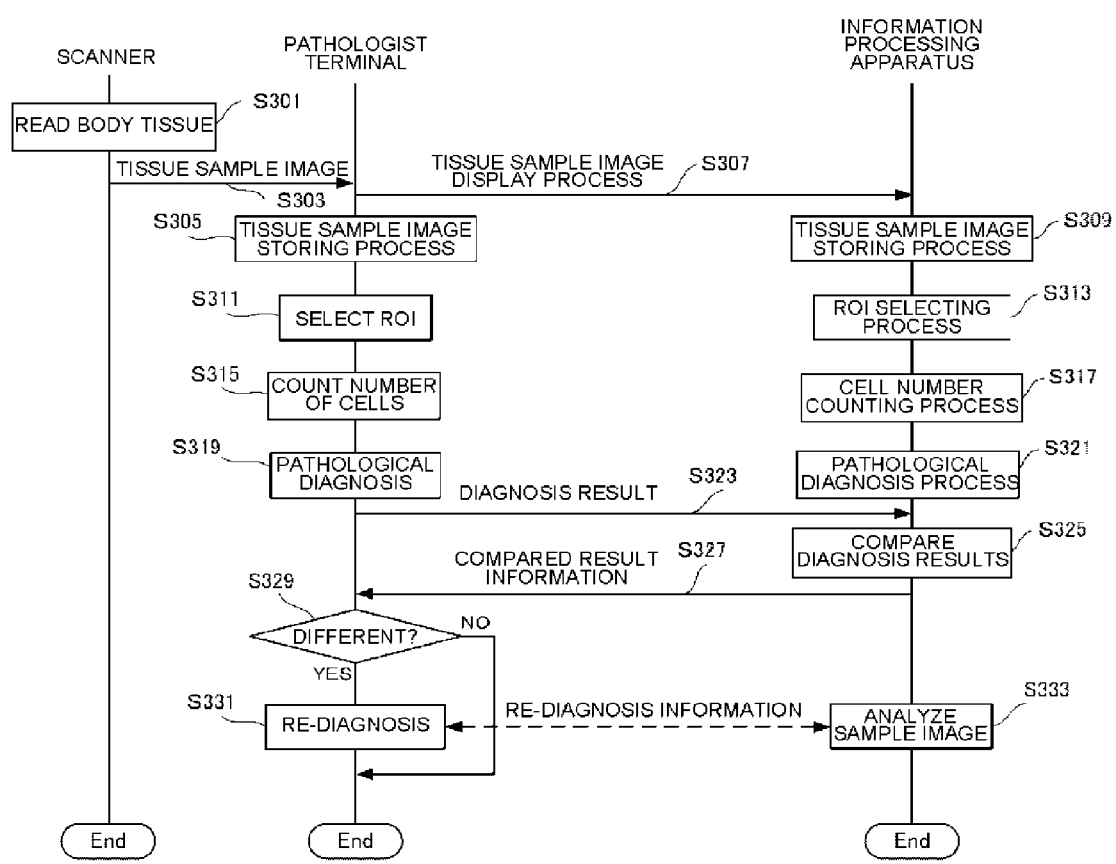
FIG. 3 is a sequence diagram showing an operation sequence of an information processing system according to the second exemplary embodiment of the present invention.

FIG. 3 is a sequence diagram showing an operation sequence of the information processing system according to the exemplary embodiment.

First, in Step S301, the pathologist 261 or 262 makes the scanner 251 or 252 read slides of the body tissue in the pathologist terminal 221 or 222. In Step S303, tissue sample images are transmitted to the pathologist terminal 221 or 222 from the scanner 251 or 252. In Step S305, the tissue sample images are transmitted to the information processing apparatus 210 from the pathologist terminal 221 or 222.

The pathologist 261 or 262 performs a pathological diagnosis with referring to the tissue sample images on the display device 231 or 232. Step S307 is a process in which the pathologist terminal 221 or 222 displays the images received from the scanner 251 or 252 on the display device 231 or 232. Steps S311, S315, and S319 are operation sequences of the pathological diagnosis performed by the pathologist 261 or 262. In Step S311, the ROIs are selected by referring to low-resolution tissue sample images displayed on the display device 231 or 232. Next, in Step S315, the number of cancer cells in each ROI is counted by referring high-resolution tissue sample images displayed on the display device 231 or 232. Finally, in Step S319, the pathological diagnosis, by which whether negative or positive is determined, is performed based on the number of cancer cells in each ROI. In addition, the pathologist 261 or 262 can request for supporting of the information processing apparatus 210 for selecting ROI or counting the number of cancer cells in each ROI at the time of the pathological diagnosis. However, the processes are not essential and thus will not be described.

On the other hand, the information processing apparatus 210 stores body tissue images transmitted from the pathologist terminal 221 or 222, in Step S309. In the same manner as the pathologist 261 or 262, ROIs are selected in Step S313 and the number of cancer cells in each ROI is counted in Step S317. In Step S321, the pathological performs diagnosis, by which it is determined whether negative (hereinafter, abbreviated as N in some cases) or positive (herein, abbreviated as P in some cases) based on the number of cancer cells in each ROI.

In Step S323, the pathological diagnosis result of the pathologist 261 or 262 is transmitted to the information processing apparatus 210 from the pathologist terminal 221 or 222. The information processing apparatus 210 that receives the pathological diagnosis result of the pathologist 261 or 262 compares the pathological diagnosis result of the pathologist 261 or 262 and the pathological diagnosis result of the information processing apparatus 210, in Step S325. In Step S327, the information corresponding to the compared result is transmitted to the pathologist terminal 221 or 222. The information corresponding to the compared result will be described with reference to FIG. 7.

The pathologist terminals 221 or 222 that receives the compared result and the information corresponding to the compared result, determines the compared result in Step S329. Generally, the terminals determine whether the pathological diagnosis result of the pathologist 261 or 262 and the pathological diagnosis result of the information processing apparatus 210 are the same as or different from each other. In a case where they are different from each other, re-diagnosis is performed for final diagnosis in Step S331. In the re-diagnosis, a request for acquiring information for the re-diagnosis is transmitted to the information processing apparatus 210 if necessary. The information processing apparatus 210 further analyzes the sample images in Step S333, and replies to the pathologist terminal 221 or 222. On the other hand, in a case where the results are the same as each other, the diagnosis result is confirmed and the post process is further performed (see FIG. 7).

Although not shown in FIG. 3 to avoid complication, in a case where the pathological diagnosis result of the pathologist 261 or 262 and the pathological diagnosis result of the information processing apparatus 210 are different from each other, it is possible that transmitting the tissue sample image to the specialist terminal 270 and requesting for the diagnosis performed to the specialist 280.

<<Transition of Display Screen of Pathologist Terminal>>

Hereinafter, transition of display screens of the display device 231 or 232 of the pathologist terminal 221 or 222 of the exemplary embodiment according to the operation sequence will be described. Note that, display screens in FIGS. 4A to 4D are examples, and the display screens are not limited thereto.

(Initial Screen)

Figure 4A:
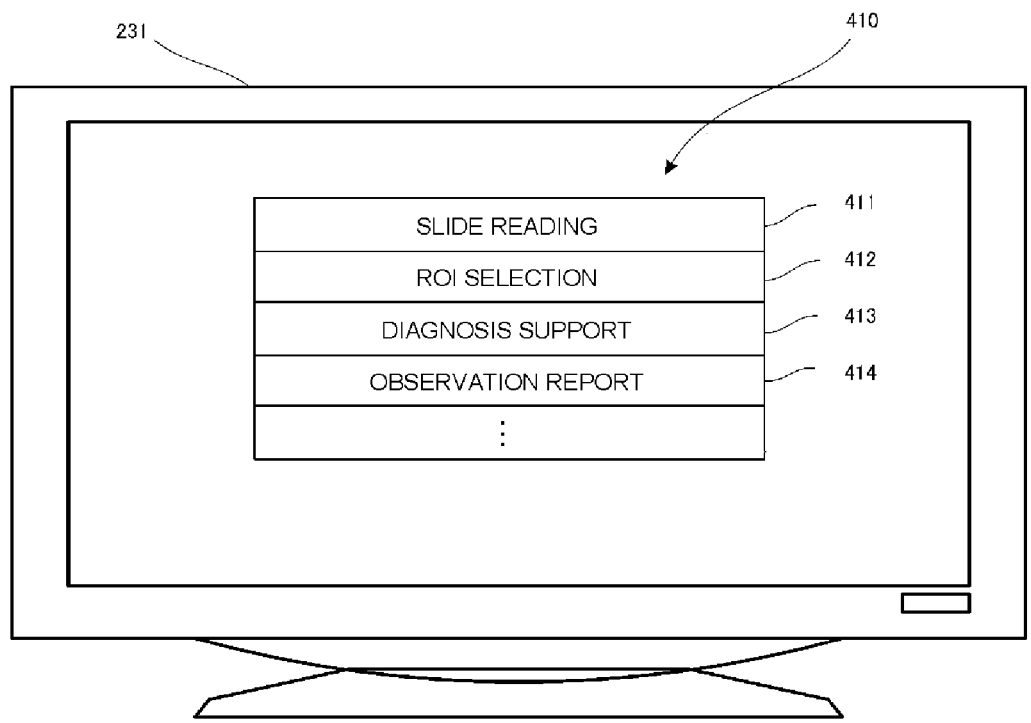
FIG. 4A is a view showing an initial screen of a pathologist terminal according to the second exemplary embodiment of the present invention.

FIG. 4A is a view showing an initial screen of the pathologist terminal 221 or 222 according to the exemplary embodiment. FIGS. 4A to 4D show only the display device 231.

An initial menu 410 is shown in FIG. 4A. The following four menus are included in the initial menu 410. First, "slide reading" 411 for designating slide reading using the scanner is included. "ROI selection" 412 for displaying the tissue sample image and receiving the ROI selection is included. "Diagnosis support" 413 for requesting a support of the information processing apparatus 210 at the time of the pathological diagnosis is included. In addition, "observation report" 414 for transmitting the diagnosis result of a pathologist and requesting comparison of the transmitted diagnosis result and the diagnosis result of the information processing apparatus is included.

(Body Tissue Display Screen)

Figure 4B:
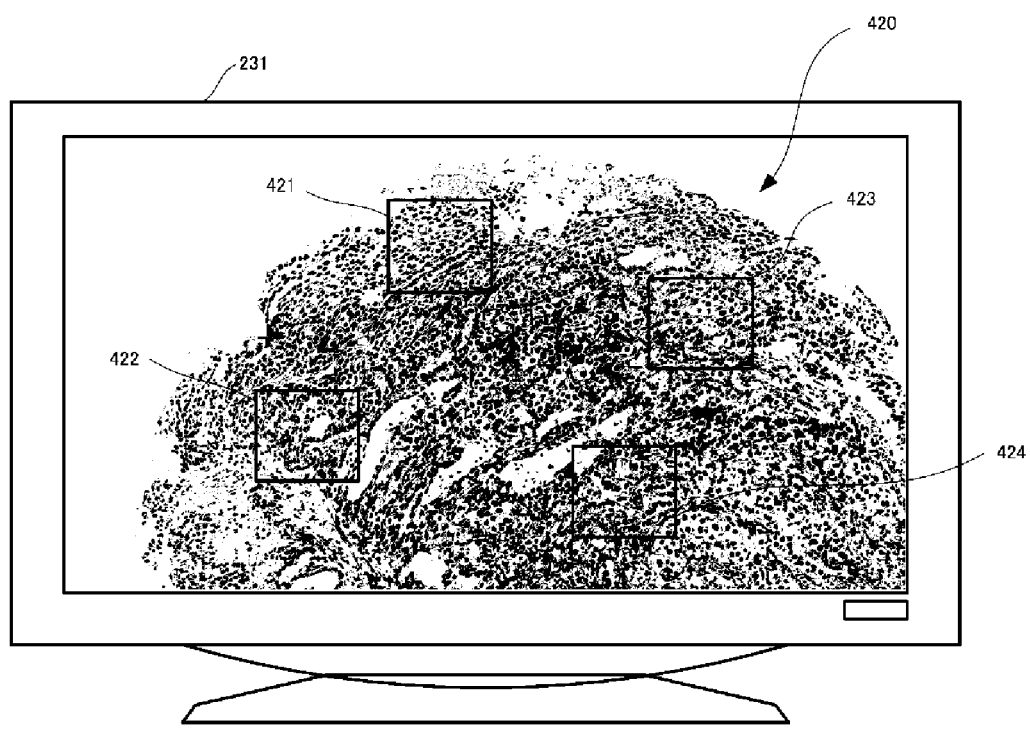
FIG. 4B is a diagram showing a body tissue display screen of a pathologist terminal according to the second exemplary embodiment of the present invention.

FIG. 4B is a view showing a body tissue display screen of the pathologist terminal 221 or 222 according to the exemplary embodiment.

FIG. 4B is a display screen in a case of designating the "ROI selection" 412 after performing the slide reading. On the display device 231, a tissue sample image 420 is displayed, and positions of four ROI 421 to 424 that the pathologist 261 selected are displayed. The pathologist 261 selects whether to count the number of cancer cells by herself or to count the number of cancer cells by using the information processing apparatus 210. In a case where the pathologist 261 counts the number of cancer cells in ROI by herself, each of ROIs 421 to 424 is zoomed in and displayed from FIG. 4B. On the other hand, in a case of receiving support by requesting the information processing apparatus 210 for counting the number of cancer cells in the ROI, a position coordinate of each ROI is transmitted to the information processing apparatus 210.

(Diagnosis Result Input Screen)

Figure 4C:
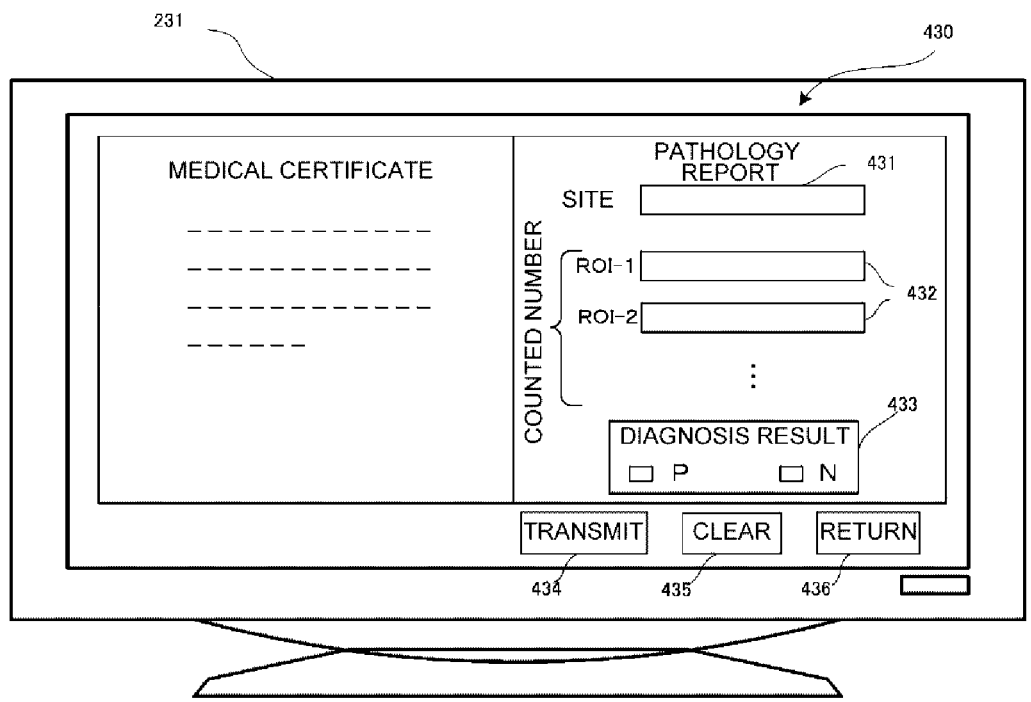
FIG. 4C is a view showing a diagnosis result input screen of a pathologist terminal according to the second exemplary embodiment of the present invention.

FIG. 4C is a view showing a diagnosis result input screen of the pathologist terminal 221 or 222 according to the exemplary embodiment.

FIG. 4C is a display screen of the display device 231 at the time when the pathologist 261 finishes a pathological diagnosis, the result is transmitted to the information processing apparatus 210, and a comparison of the result and the diagnosis result of the information processing apparatus 210 is requested. A format 430 formed of a medical certificate and a pathology report transmitted from the information processing apparatus 210 is displayed on the display device 231. It is the pathology report to which the pathologist 261 inputs the pathological diagnosis.

At least, a site of a pathological diagnosis 431, counted numbers of cancer cells of each selected ROI 432, and a diagnosis result (P: Positive, N: Negative) 433 are input to the pathology reporter. Although not shown in FIG. 4C, by the processes so far, information items necessary for the pathological diagnosis such as a pathologist ID, a tissue sample image ID, an ROI ID and a position thereof, gender and age of a patient, and the like are held in the pathologist terminal 221 or 222, and are also transmitted to the information processing apparatus 210.

When a transmission button 434 is designated, the report is transmitted to the information processing apparatus 210. In addition, when a clear button 435 is designated, the parts of the report can be input again. When a return button 436 is designated, the screen returns to the previous screen (for example, FIG. 4B or 4A).

(Compared Result Informing Screen)

Figure 4D:
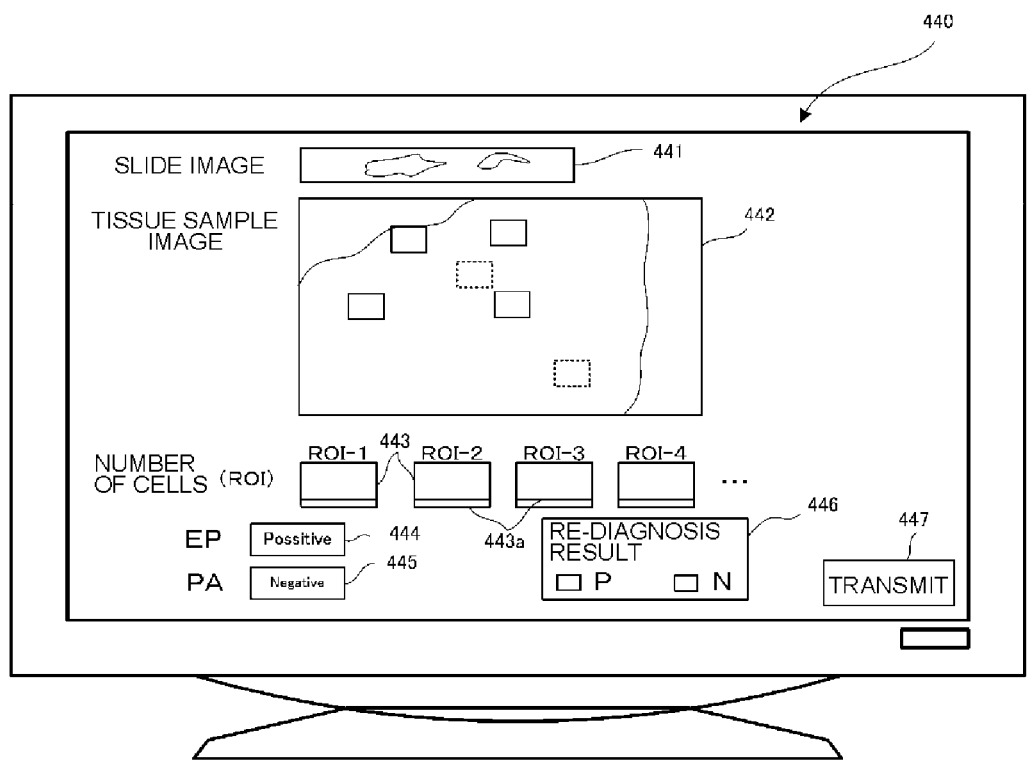
FIG. 4D is a view showing a compared result informing screen of a pathologist terminal according to the second exemplary embodiment of the present invention.

FIG. 4D is a view showing a compared result informing screen of a pathologist terminal 221 or 222 according to the exemplary embodiment.

FIG. 4D is an informing screen which informs the compared result of the diagnosis results transmitted from the information processing apparatus 210, and at the same time, is an input screen for a later process (also called a post process) in a case where both the diagnosis results are P (Positive) or in a case where both the diagnosis results are different from each other.

For informing, a slide image 441 that is read at the time of starting the pathological diagnosis, a tissue sample image 442 in which the ROI (rectangles with a solid line) selected by the information processing apparatus 210 are displayed in an overlapped manner, and each ROI 443 are displayed. The number of cancer cells that is ranked with positivity grade may be displayed as a visually recognizable bar graph 443a or the like on each ROI 443. In addition, a diagnosis result 444 of the information processing apparatus 210 (hereinafter, also referred to as e-Pathologist (EP)) and a diagnosis result 445 of the pathologist 261 or 262 (hereinafter, also referred to as Pathologist (PA)) are displayed.

In order for inputting, an ROI (rectangles with a dashed line), which is a part of ROIs selected by the pathologist 261 from the tissue sample image 442 and which is selected for requesting the information processing apparatus 210 for analysis, is displayed. This selection of the ROI is, in particular, for an operation with which the information processing apparatus 210 performs a re-analysis of the ROI determined as positive by the pathologist 261 in a case where the EP is negative and the PA is positive. In addition, in a case where the diagnosis results are different from each other, a re-diagnosis result 446 to be input by the pathologist 261 is displayed by referring to the result of the re-analysis performed by the pathologist 261 and the information processing apparatus 210. In addition, a transmission button 447 for transmitting the input information from the screen of FIG. 4D to the information processing apparatus 210 is displayed.

<<Hardware Configuration of Information Processing Apparatus>>

Figure 5:
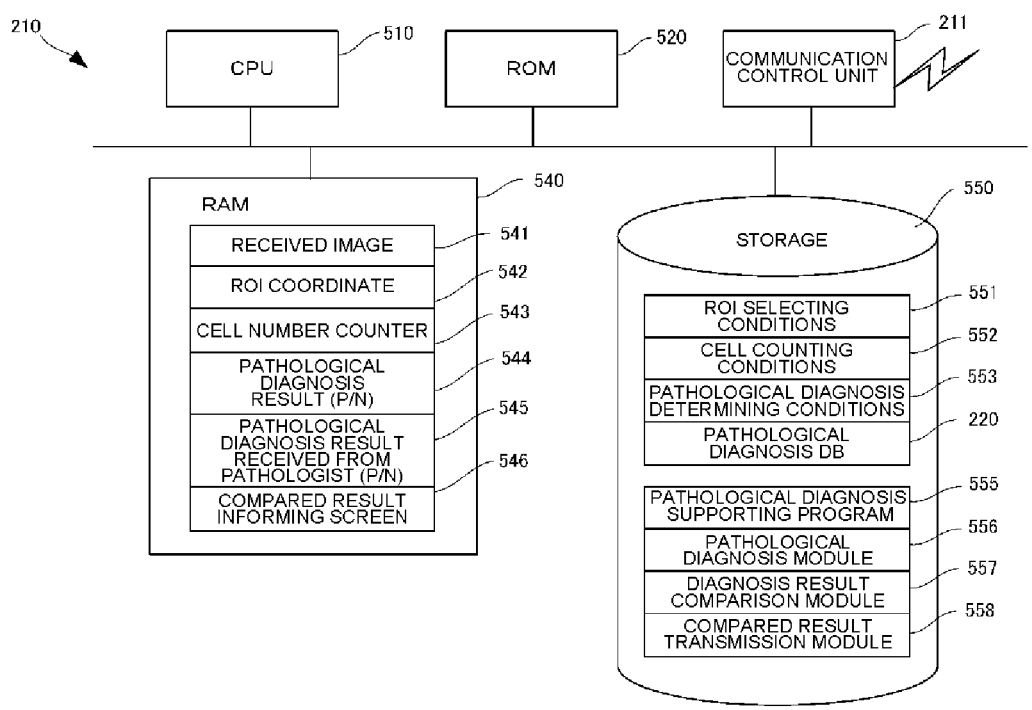
FIG. 5 is a block diagram showing a hardware configuration of an information processing apparatus according to the second exemplary embodiment of the present invention.

FIG. 5 is a block diagram showing a hardware configuration of the information processing apparatus 210 according to the exemplary embodiment.

In FIG. 5, a CPU 510 is a processor for arithmetic control, and performs control of the information processing apparatus 210 by executing a program. An ROM 520 is a read-only memory which stores initial data, a program, and static data used by a program. The program may be stored in storage 550 or the like, and is not necessarily stored in the ROM 520. The communication control unit 211 controls communication with the plurality of pathologist terminals 221 and 222 or the specialist terminal 270 through the network 290. Such communication may be performed in a wired or wireless manner.

An RAM 540 is a random access memory used as a work area for temporary storage by the CPU 510. An area for storing data necessary for realization of the exemplary embodiment is secured in the RAM 540. A medical consultation image 541 which is a tissue sample image received from the pathologist terminal 221 or 222 is stored in each area. An ROI coordinate 542 that is position information of the ROI set as an analysis target in the tissue sample image by the information processing apparatus 210 is stored therein. A cell number counter 543 is used for counting cancer cells in each ROI by the information processing apparatus 210 therein. A pathological diagnosis result (P/N) 544 performed by the information processing apparatus 210 is stored therein. A pathological diagnosis result (P/N) 545 transmitted by the pathologist 261 or 262 is stored therein. In addition, a compared result informing screen 546 that is generated corresponding to the compared result and is transmitted to the pathologist terminal 221 or 222 is stored therein.

The storage 550 is a non-volatile mass storage device that stores a database, various parameters and programs executed by the CPU 510. The following data or programs necessary for implementing the exemplary embodiment is stored in the storage 550. The data memory unit stores ROI selecting conditions 551 for selecting the ROI by the information processing apparatus 210. The data memory unit stores cell counting conditions 552 for recognizing and counting cancer cells by the information processing apparatus 210. The data memory unit stores pathological diagnosis determining conditions 553 for determining pathological diagnosis results (P/N) by the information processing apparatus 210. In addition, the data memory unit stores the pathological diagnosis DB 220 for accumulating the diagnosis results of the pathologist, the diagnosis results of the information processing apparatus, the compared results, and the final results, in association with the tissue sample image.

Figure 7:
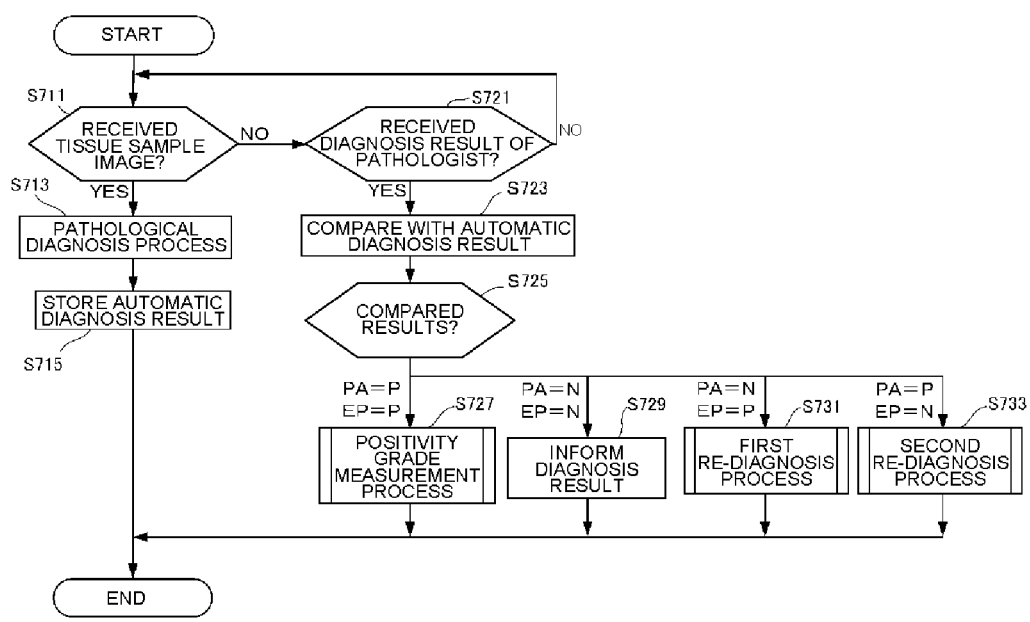
FIG. 7 is a flowchart showing a process sequence of an information processing apparatus according to the second exemplary embodiment of the present invention.

A program memory unit stores a pathological image diagnosis supporting program 555 that implements a series of pathological image diagnosis supporting (see FIG. 7). In addition, the program memory unit stores a pathological diagnosis module 556, a diagnosis result comparison module 557, and a compared result transmission module 558 that are used by the pathological image diagnosis supporting program 555. The pathological diagnosis module 556 performs selection of ROI from the tissue sample image, counting of cancer cells, and a pathological diagnosis. In addition, the diagnosis result comparison module 557 performs comparison of the pathological diagnosis results by each of the pathologist 261 and the information processing apparatus 210. The compared result transmission module 558 generates a display screen and transmits the analyzed result.

FIG. 5 only shows necessary data or a program for the exemplary embodiment, and does not show general-purpose data or programs such as OS.

(Pathological Diagnosis DB)

Figure 6:
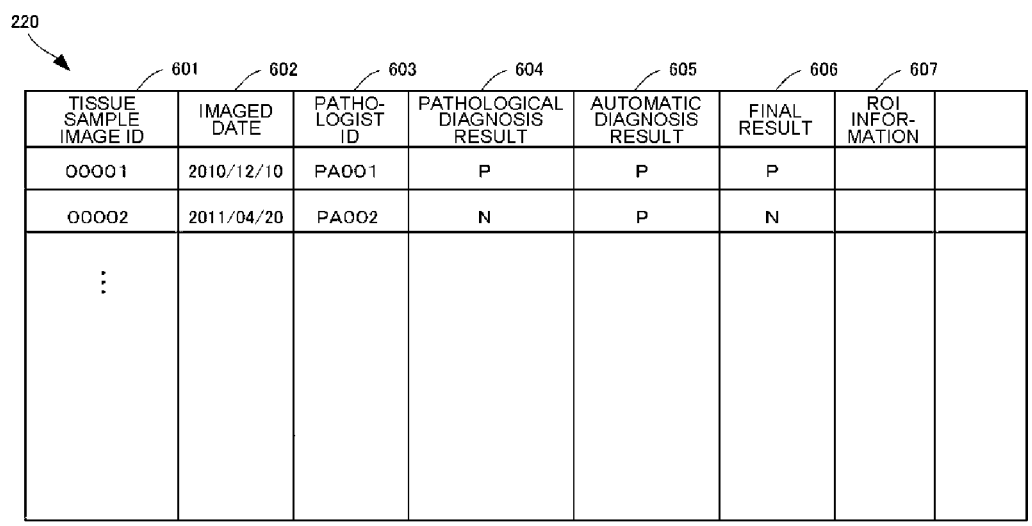
FIG. 6 is a view showing a configuration of a pathological diagnosis DB according to the second exemplary embodiment of the present invention.

FIG. 6 is a view showing a configuration of the pathological diagnosis DB 220 according to the exemplary embodiment.

The pathological diagnosis DB 220 accumulates the diagnosis results of the pathologist, the diagnosis results of the information processing apparatus, the compared results, and the final results, in association with the tissue sample image. As shown in FIG. 6, imaged date 602 and a pathologist ID 603 are stored in association with a tissue sample image ID 601. In addition, a pathological diagnosis result 604 that is the diagnosis result of the pathologist, an automatic diagnosis result 605 that is the diagnosis result of the information processing apparatus 210, and a final result 606 are stored. Further, ROI information 607 of the diagnosis target is stored.

The data accumulated in the pathological diagnosis DB 220 is not limited to FIG. 6. For example, information that helps enhancement of various pathological diagnoses based on the history such as information of a patient who is a diagnosis target, or aversion of the pathological diagnosis program of the information processing apparatus may be accumulated.

<<Process Sequence of Information Processing Apparatus>>

FIG. 7 is a flowchart showing a process sequence of the information processing apparatus 210 according to the exemplary embodiment. The process of this flowchart is executed by the CPU 510 of FIG. 5 using the RAM 540, and realizes each functional configuration unit of the information processing apparatus 210.

First, in Step S711, it is determined whether or not it is the reception of the tissue sample image from the pathologist terminal. If it is determined that it is the reception of the tissue sample image, the process proceeds to Step S713, and the pathological diagnosis process including ROI selection, cancer cell counting, and the pathological diagnosis is performed. In Step S715, the result of the pathological diagnosis process in Step S713 is stored in the pathological diagnosis result 544 with the ROI and the like as the automatic diagnosis result.

If it is determined that it is not the reception of the tissue sample image, in Step S721, it is determined whether or not it is the reception of the diagnosis result from the pathologist. If it is determined that it is the reception of the diagnosis result from the pathologist, the process proceeds to Step S723, and the diagnosis result is acquired from the pathological diagnosis result DB 220, which result is performed by the information processing apparatus 210 with respect to the tissue sample image that is set as a target by the diagnosis result by the pathologist received in Step S721. Further, the acquired pathological diagnosis result by the information processing apparatus 210 and the diagnosis result by the pathologist received in Step S721 are compared, and the process proceeds to Step S725. In Step S725, the process is divided into four processes corresponding to the compared result.

Figure 8B:
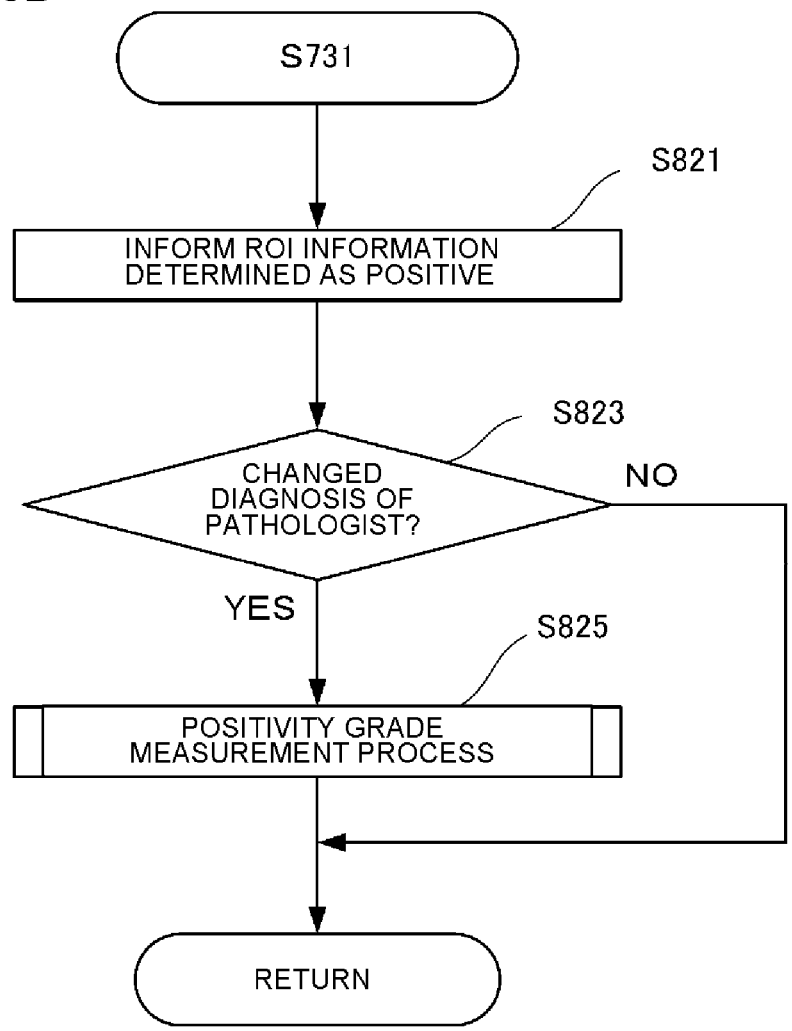
FIG. 8B is a flowchart showing a process sequence of a first re-diagnosis process according to the second exemplary embodiment of the present invention.

First, in a case where both the PA and the EP are positive, the process proceeds to Step S727, and a positivity grade measurement process for measuring a positivity grade is further performed (see FIG. 8A). Next, in a case where both the PA and the EP are negative, the process proceeds to Step S729, and the diagnosis results are informed to the pathologist 261, as they are. In addition, in a case where the PA is negative and the EP is positive, the process proceeds to Step S731, and the ROI that is determined as positive by the information processing apparatus 210 is informed to the pathologist 261, and a re-diagnosis by the pathologist 261 is performed (see FIG. 8B). Next, in a case where the PA is positive and the EP is negative, the process proceeds to Step S733, and the ROI that is determined as positive by the pathologist 261 is transmitted to the information processing 210, and a re-diagnosis by the information processing apparatus 210 is performed (see FIG. 8C).

By transmitting the informing information corresponding to the compared results of the diagnosis results described above to the pathologist terminal, the subsequent process (post process) can be rapidly performed.

(Positivity Grade Measurement Process)

FIG. 8A is a flowchart showing a process sequence of the positivity grade measurement process (S727) according to the exemplary embodiment. This process is a process to be performed in a case where both the PA and the EP are positive.

First, in Step S811, the ROI information selected by the information processing apparatus 210 and the analysis results (the counted number of the cancer cells, and the like) are informed to the pathologist terminal 241 (see FIG. 4D). In Step S813, it is determined whether or not there is a request of the ROI analysis necessary for further determination of the positivity grade in detail. If it is determined that there is a request, the process proceeds to Step S815, and the ROI that is requested for analysis, is analyzed. Then, in Step S817, the analyzed result is informed to the pathologist 261. The added analysis is repeated as needed. If it is determined that there is no request, the positivity grade measurement process is finished and the process is returned.

(First Re-Diagnosis Process)

FIG. 8B is a flowchart showing a process sequence of a first re-diagnosis process (S731) according to the exemplary embodiment. This process is a process to be performed in a case where the PA is negative and the EP is positive.

First, in Step S821, ROI information of the target that is determined as positive is informed to the pathologist 261 (see FIG. 4D). In Step S823, results obtained by re-diagnosis by the pathologist 261 based on the informed ROI information is received. In a case where the re-diagnosis result by the pathologist 261 is positive, the process proceeds to Step S825, and the process of the positivity grade measurement process (S727) of FIG. 8A is performed. Herein, the description of the process of FIG. 8A is not repeated. In a case where the re-diagnosis result by the pathologist 261 is negative, the first re-diagnosis process is finished and the process is returned.

(Second Re-Diagnosis Process)

Figure 8C:
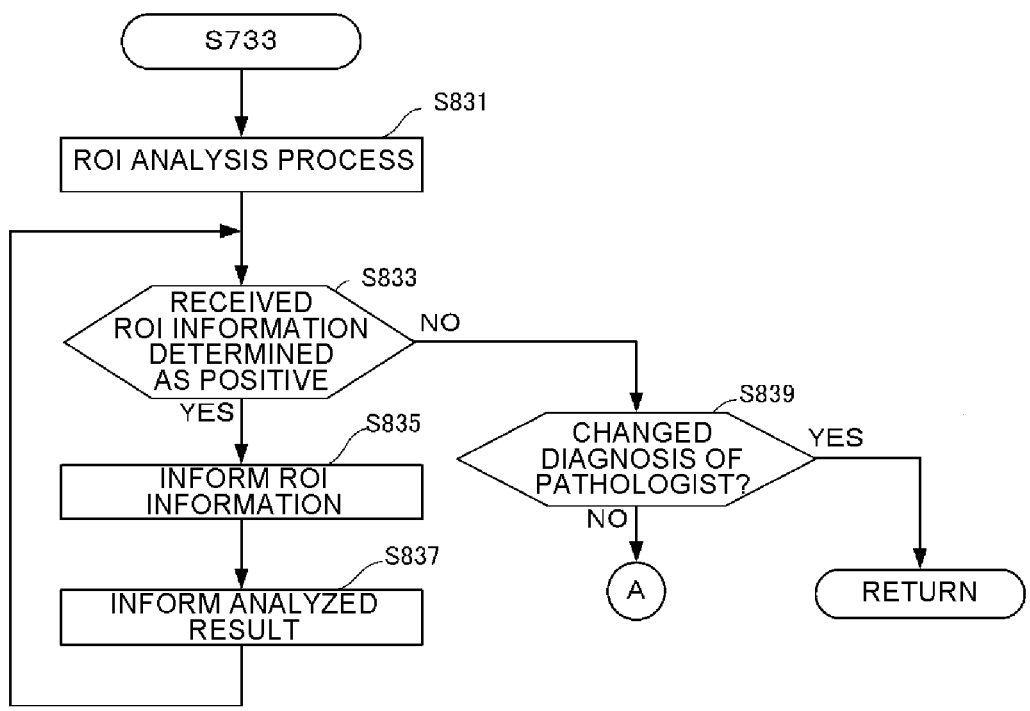
FIG. 8C is a flowchart showing a process sequence of a second re-diagnosis process according to the second exemplary embodiment of the present invention.

FIG. 8C is a flowchart showing a process sequence of a second re-diagnosis process (S733) according to the exemplary embodiment. This process is a process to be performed in a case where the PA is positive and the EP is negative.

First, in Step S831, the ROI information analyzed by the information processing apparatus 210 is informed to the pathologist 261. In Step S833, the ROI information of the target diagnosed as positive by the pathologist 261 is received. If the ROI information of the target diagnosed as positive by the pathologist 261 is received, the process proceeds to Step S835, and the analysis of the ROI thereof is performed. Then, in Step S837, the analysis results are informed to the pathologist 261. If the reception of the ROI information of the target diagnosed as positive by the pathology 261 is finished, the process proceeds to the Step S839, and the results of the re-diagnosis performed by the pathologist 261 based on the analysis results informed in Step S837 is received. In a case where the result of the re-diagnosis by the pathologist 261 is still positive (P) as the initial diagnosis results, the final result is determined as positive. The process proceeds to Step S813 of FIG. 8A, another ROI analysis for positivity grade measurement is performed, and the process is returned. In a case where the results of the re-diagnosis of the pathologist 261 is negative (N) changed from the initial diagnosis results, the final result is determined as negative, the second re-diagnosis process is finished, and the process is returned.

In a real-world process, after each of final diagnosis results is determined, the EP may need approval of a division manager (DM). This process can also be automated so as to transmit the final diagnosis result from the information processing apparatus 210 to a DM terminal, and obtain the approval. Alternatively, there may be a further request of a diagnosis to the other pathologist or specialist from the DM for confirmation. However, the processes are not described in detail using the drawings.

Third Exemplary Embodiment

Next, an information processing system according to a third exemplary embodiment of the present invention will be described. Compared to the second exemplary embodiment, an information processing system of this exemplary embodiment is different in that it further includes a pathologist diagnosis tendency extraction unit which extracts tendency of a pathological diagnosis of a pathologist by using a pathological diagnosis history accumulated in the pathological diagnosis DB 220. The pathologist diagnosis tendency from the pathologist diagnosis tendency extraction unit may be, for example, used as information for the pathologist selection by informing to the DM described above, or may be used as information for study of a pathologist while referring to her tendency. According to the exemplary embodiment, the diagnosis tendency of the pathologist can be analyzed. Since the exemplary embodiment is basically the same as the second exemplary embodiment except for additional portions to be described later, the description will not be repeated.

<<Configuration of Information Processing System>>

Figure 9:
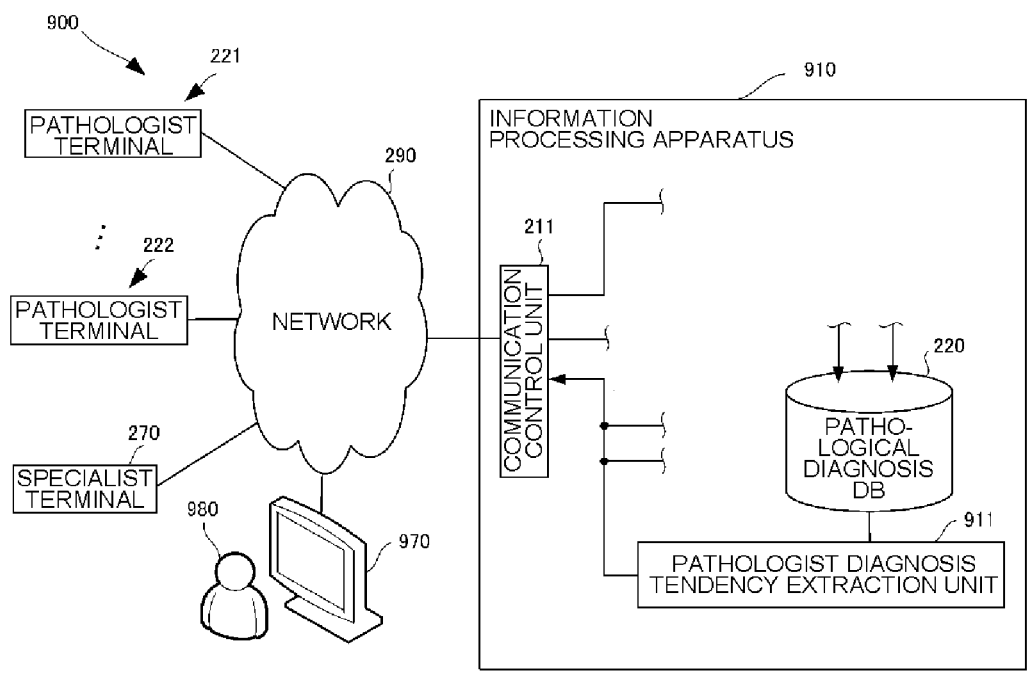
FIG. 9 is a block diagram showing a configuration of an information processing system according to a third exemplary embodiment of the present invention.

FIG. 9 is a block diagram showing a configuration of an information processing system 900 according to the exemplary embodiment. The additional portions in the configuration of FIG. 9 comparing to FIG. 2 will be described.

First, in a configuration of an information processing apparatus 910, a pathologist diagnosis tendency extraction unit 911 is provided, which reads out accumulated data from the pathological diagnosis DB 220 and generates pathologist diagnosis tendency information. The other configuration and the operations are the same as those of the second exemplary embodiment, and thus are not shown in the drawing to avoid making the drawing complicated.

Other than the pathologist terminals 221 and 222 or the specialist terminal 270 of FIG. 2, a DM terminal 970 and a DM 980 are shown through the network 290.

(Pathologist Diagnosis Tendency Information)

FIG. 10 is a block diagram showing a configuration of pathologist diagnosis tendency information 1000 according to the exemplary embodiment. This information is generated from the accumulated data that the pathologist diagnosis tendency extraction unit 911 reads out from the pathological diagnosis DB 220.

In the pathologist diagnosis tendency information 1000, the following information is stored in association with a pathologist ID 1001, a site 1002, and a diagnosis date 1003. That is, a pathologist diagnosis result 1004 that is the diagnosis result of the PA, an automatic diagnosis result 1005 that is the diagnosis result of the EP, and a final result 1006 are stored. In addition, a pathologist ROI 1007 that is the ROI selected by the PA, an automatic ROI 1008 that is the ROI selected by the EP, and a ROI 1009 that is used in the final result, are stored.

Further, an evaluation value 1010 of a pathologist in each diagnosis is stored. Such an evaluation value 1010 may be a value input by the DM or may be automatically set from the relationship between the initial diagnosis result and the final diagnosis result. The pathologist diagnosis tendency extraction unit 911 performs diagnosis tendency of a pathologist or diagnosis evaluation, based on a high or low level of the evaluation value or the deviation of the difference of sites.

Fourth Exemplary Embodiment

Next, an information processing system according to a fourth exemplary embodiment of the present invention will be described. In the information processing system according to the exemplary embodiment, a study is performed for improving accuracy of the pathological diagnosis of the EP in a pathological diagnosis study unit using the accumulated data in the pathological diagnosis DB 220, compared to the second exemplary embodiment. The information processing system according to the exemplary embodiment is different from that of the second exemplary embodiment, in that the results of the study are fed back to the ROI selection unit, the cell number counting unit, or the pathological diagnosis unit. According to the exemplary embodiment, it is possible to improve the diagnosis accuracy of the EP by accumulating the diagnosis results of the PA and the EP, particularly from a difference with the diagnosis result of the EP in a case where the PA is an experienced specialist.

<<Configuration of Information Processing System>>

Figure 11:
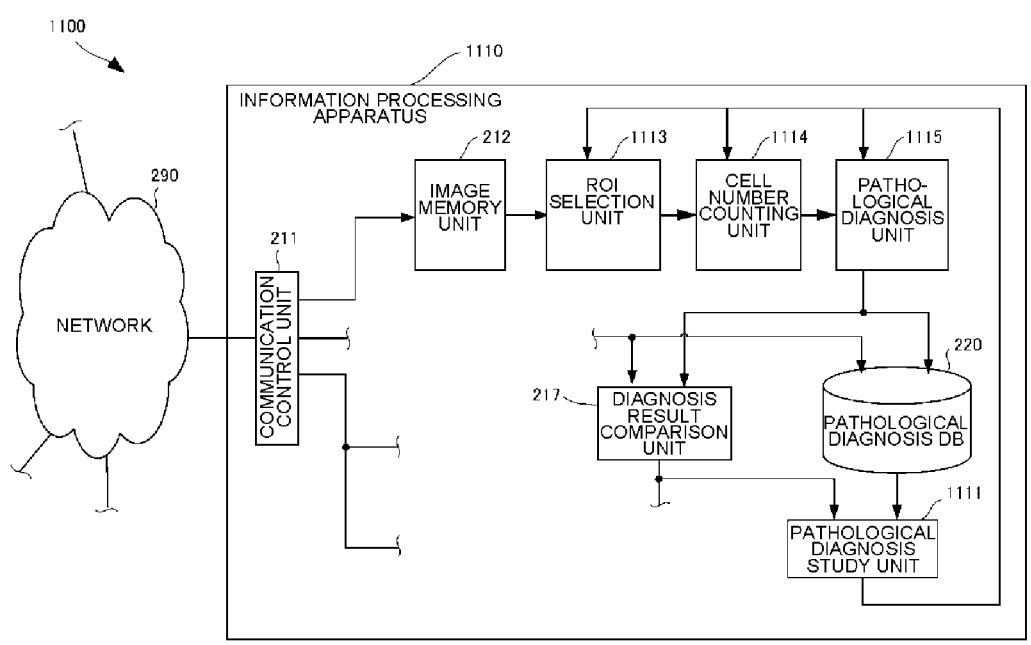
FIG. 11 is a block diagram showing a configuration of an information processing system according to a fourth exemplary embodiment of the present invention.

FIG. 11 is a block diagram showing a configuration of an information processing system 1100 according to the exemplary embodiment.

An information processing apparatus 1110 of FIG. 11 includes a pathological diagnosis study unit 1111 which performs updating of the configuration units regarding the pathological diagnosis, based on the information from the pathological diagnosis DB 220 and the diagnosis result comparison unit 217. According to the studied results, the pathological diagnosis study unit 1111 updates the control of a ROI selection unit 1113, a cell number counting unit 1114, or a pathological diagnosis unit 1115 by sending control parameters to them. The control parameters may be used for updating the ROI selection conditions 551, the cell counting conditions 552, and the pathological diagnosis determining conditions 553 shown in FIG. 5. Alternatively, the control parameters may be used for the changing, adding, and deleting of the control program of each unit, or the changing, adding, and deleting of algorithms.

In addition, the other configuration and the operation are the same as those of the second exemplary embodiment, and the drawings and the detailed descriptions thereof will be not repeated for avoiding making the drawing complicated.

Other Exemplary Embodiment

Hereinabove, the exemplary embodiments of the present invention have been described, and a system or an apparatus in which each characteristic included in each exemplary embodiment is combined in any formats, is also included in the scope of the present invention.

In addition, the present invention may be applied to a system configured of a plurality of devices or may be applied to a single device. Further, the present invention can be applied even in a case where a control program for implementing the functions of the exemplary embodiments is supplied directly or remotely to a system or a device. Accordingly, a control program that is installed in a computer, a medium that stores the control program, and even a World Wide Web (WWW) server for downloading the control program, for implementing the functions of the present invention in the computer, are included in the scope of the present invention.

This application is based upon and claims the benefit of priority from Japanese patent Application No. 2011-111707, filed on May 18, 2011; the entire contents of which are incorporated herein by reference.

The invention claimed is:

1. An information processing system which supports a pathological diagnosis based on tissue sample image data obtained by imaging a body tissue, the system comprising:
a pathological diagnosis apparatus comprising a processor configured to perform a pathological diagnosis based on a plurality of first regions of interest of the tissue sample image data and output a first pathological diagnosis result indicating positive or negative for a disease, the plurality of the first regions of interest being respective ones of partial regions of the tissue sample image data; and
a pathologist terminal comprising a processor configured to receive input indicating a second pathological diagnosis result obtained by a pathological diagnosis performed by a pathologist based on the tissue sample image data, the second pathological diagnosis result indicating positive or negative for the disease,
wherein the pathological diagnosis apparatus is further configured to:
compare the first pathological diagnosis result and the second pathological diagnosis result and output a third result for the disease based on the comparison;
when both the first pathological diagnosis result and the second pathological diagnosis result indicate positive, perform an image analysis of the tissue sample image data to calculate a positivity grade of disease based on the tissue sample image data, and output the third result indicating the positivity grade of disease;
when both the first pathological diagnosis result and the second pathological diagnosis result indicate negative, output the third result indicating negative for the disease without performing the image analysis of the tissue sample image data to calculate the positivity grade of disease;
when the first pathological diagnosis result indicates negative and the second pathological diagnosis result indicates positive, output the third result indicating one or more of the plurality of first regions of interest of the tissue sample image data each of which is determined as negative for disease by the pathological diagnosis apparatus; and
when the first pathological diagnosis result indicates positive and the second pathological diagnosis result indicates negative, output the third result indicating one or more of the plurality of first regions of interest of the tissue sample image data each of which is determined as positive for disease by the pathological diagnosis apparatus.

2. The information processing system according to claim 1, wherein the pathological diagnosis apparatus is further configured to set a second region of interest of the tissue sample image data and perform the pathological diagnosis based on a number of cancer cells in the second region of interest.

3. The information processing system according to claim 1, wherein the pathological diagnosis apparatus is further configured to:
receive a setting of a second region of interest of the tissue sample image data; and
analyze the set second region of interest of the tissue sample image data.

4. The information processing system according to claim 1, wherein the pathological diagnosis apparatus is further configured to:
receive identification of a second region of interest of the tissue sample image data determined as positive by the pathologist; and
analyze the second region of interest of the tissue sample image data.

5. The information processing system according to claim 1, wherein the pathological diagnosis apparatus comprises a database which accumulates a history of the first pathological diagnosis result and the second pathological diagnosis result in association with the tissue sample image data, and the pathological diagnosis apparatus is further configured to update a diagnostic method for the disease based on the history accumulated in the database.

6. The information processing system according to claim 1, wherein the pathological diagnosis apparatus comprises a database which accumulates a history of comparison of the first pathological diagnosis result and the second pathological diagnosis result in association with the pathologist who performed the pathological diagnosis, and the pathological diagnosis apparatus is further configured to determine a diagnostic tendency of the pathologist from the history of comparison accumulated in the database.

7. The information processing system according to claim 1, further comprising:
an imaging device configured to image the body tissue to generate the tissue sample image data;
a display configured to display the tissue sample image data; and
a transmission device configured to transmit the tissue sample image data to the pathological diagnosis apparatus.

8. An information processing method for supporting a pathological diagnosis based on tissue sample image data obtained by imaging a body tissue, the method comprising:
receiving the tissue sample image data;
performing, by one or more processors, a pathological diagnosis based on the tissue sample image data and outputting a first pathological diagnosis result indicating positive or negative for a disease;
receiving input indicating a second pathological diagnosis result obtained by a pathological diagnosis performed by a pathologist based on the tissue sample image data, the second pathological diagnosis result indicating positive or negative for the disease;
comparing, by the one or more processors, the first pathological diagnosis result and the second pathological diagnosis result;
outputting, by the one or more processors, a third result for the disease based on the comparison;
when both the first pathological diagnosis result and the second pathological diagnosis result indicate positive, performing an image analysis of the tissue sample image data to calculate measuring a positivity grade of disease based on by analyzing the tissue sample image data, and outputting the third result indicating a result of the measurement of the positivity grade of disease;
when both the first pathological diagnosis result and the second pathological diagnosis result indicate negative, outputting the third result indicating negative for the disease without performing the image analysis of the tissue sample image data to calculate the positivity grade of disease;
when the first pathological diagnosis result indicates negative and the second pathological diagnosis result indicates positive, outputting the third result indicating one or more of the plurality of first regions of interest of the tissue sample image data each of which is determined as negative for disease by the pathological diagnosis apparatus; and
when the first pathological diagnosis result indicates positive and the second pathological diagnosis result indicates negative, outputting the third result indicating one or more of the plurality of first regions of interest of the tissue sample image data each of which is determined as positive for disease by the pathological diagnosis apparatus.

9. An information processing apparatus which supports a pathological diagnosis based on tissue sample image data obtained by imaging a body tissue, the apparatus comprising:
a memory storing instructions; and
a pathological diagnosis processor configured to execute the instructions to:
perform a pathological diagnosis based on the tissue sample image data and output a first pathological diagnosis result indicating positive or negative for a disease;
receive an indication of a second pathological diagnosis result obtained by a pathological diagnosis performed by a pathologist based on the tissue sample image data, the second pathological diagnosis result indicating positive or negative for the disease;
compare the first pathological diagnosis result and the second pathological diagnosis result;
output a third result for the disease based on the comparison;
when both the first pathological diagnosis result and the second pathological diagnosis result indicate positive, perform an image analysis of the tissue sample image data to calculate measure a positivity grade of disease based on by analyzing the tissue sample image data, and output the third result indicating a result of the measurement of the positivity grade of disease;
when both the first pathological diagnosis result and the second pathological diagnosis result indicate negative, output the third result indicating negative for the disease without performing the image analysis of the tissue sample image data to calculate the positivity grade of disease;
when the first pathological diagnosis result indicates negative and the second pathological diagnosis result indicates positive, output the third result indicating one or more of the plurality of first regions of interest of the tissue sample image data each of which is determined as negative for disease by the pathological diagnosis processor; and
when the first pathological diagnosis result indicates positive and the second pathological diagnosis result indicates negative, output the third result indicating one or more of the plurality of first regions of interest of the tissue sample image data each of which is determined as positive for disease by the pathological diagnosis processor.

10. A non-transitory computer-readable storage medium storing a control program that, when executed by a processor of an information processing apparatus, causes the processor to perform a method for supporting a pathological diagnosis based on tissue sample image data obtained by imaging a body tissue, the method comprising:
performing a pathological diagnosis based on the tissue sample image data and outputting a first pathological diagnosis result indicating positive or negative for a disease;
receiving an indication of a second pathological diagnosis result obtained by a pathological diagnosis performed by a pathologist based on the tissue sample image data, the second pathological diagnosis result indicating positive or negative for the disease;
comparing the first pathological diagnosis result and the second pathological diagnosis result;
outputting a third result for the disease based on the comparison;
when both the first pathological diagnosis result and the second pathological diagnosis result indicate positive, performing an image analysis of the tissue sample image data to calculate measuring a positivity grade of disease based on by analyzing the tissue sample image data, and outputting the third result indicating a result of the measurement of the positivity grade of disease;
when both the first pathological diagnosis result and the second pathological diagnosis result indicate negative, outputting the third result indicating negative for the disease without performing the image analysis of the tissue sample image data to calculate the positivity grade of disease;

when the first pathological diagnosis result indicates negative and the second pathological diagnosis result indicates positive, outputting the third result indicating one or more of the plurality of first regions of interest of the tissue sample image data each of which is determined as negative for disease by the processor; and when the first pathological diagnosis result indicates positive and the second pathological diagnosis result indicates negative, outputting the third result indicating one or more of the plurality of first regions of interest of the tissue sample image data each of which is determined as positive for disease by the processor.

* * * * *

UNITED STATES PATENT AND TRADEMARK OFFICE
CERTIFICATE OF CORRECTION

PATENT NO. : 9,786,047 B2
APPLICATION NO. : 14/117400
DATED : October 10, 2017
INVENTOR(S) : Doi Page 1 of 1

It is certified that error appears in the above-identified patent and that said Letters Patent is hereby corrected as shown below:

In the Claims

Claim 8, Column 15, Line 32, "based on by analyzing" should read --based on--.

Claim 9, Column 16, Line 12, "based on by analyzing" should read --based on--.

Claim 9, Column 16, Line 11, "to calculate measure a positivity grade" should read --to calculate measuring a positivity grade--.

Claim 10, Column 16, Line 59, "based on by analyzing" should read --based on--.

Signed and Sealed this
Twenty-fourth Day of April, 2018

Andrei Iancu
*Director of the United States Patent and Trademark Office*